(12) United States Patent
Zhou et al.

(10) Patent No.: US 12,350,518 B2
(45) Date of Patent: Jul. 8, 2025

(54) SYSTEMS AND METHODS FOR GENERATING ADAPTIVE RADIATION THERAPY PLAN

(71) Applicant: SHANGHAI UNITED IMAGING HEALTHCARE CO., LTD., Shanghai (CN)

(72) Inventors: Jingjie Zhou, Shanghai (CN); Kejun Zhao, Shanghai (CN); Xiongfeng Peng, Shanghai (CN); Zhanglong Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 383 days.

(21) Appl. No.: 17/932,664

(22) Filed: Sep. 15, 2022

(65) Prior Publication Data
US 2023/0009625 A1    Jan. 12, 2023

Related U.S. Application Data

(63) Continuation of application No. PCT/CN2020/079488, filed on Mar. 16, 2020.

(51) Int. Cl.
*A61N 5/10* (2006.01)

(52) U.S. Cl.
CPC ......... *A61N 5/1038* (2013.01); *A61N 5/1039* (2013.01); *A61N 5/1071* (2013.01)

(58) Field of Classification Search
CPC ..... A61B 6/5235; A61B 5/0036; A61B 5/055; A61B 6/582; A61B 6/0407; A61B 6/04;
(Continued)

(56) References Cited

U.S. PATENT DOCUMENTS 7,453,984 B2 * 11/2008 Chen .................... A61N 5/1049
                                                      378/92
9,844,358 B2 * 12/2017 Wiggers ................. A61B 6/588
(Continued)

FOREIGN PATENT DOCUMENTS

| CN | 110420396 A | 11/2019 |
| EP | 3264298 A1 | 1/2018 |
| WO | 20200038683 A1 | 5/2012 |

OTHER PUBLICATIONS

The Extended European Search Report in European Application No. 20925048.9 mailed on Mar. 17, 2023, 8 pages.
(Continued)

*Primary Examiner* — Irakli Kiknadze
(74) *Attorney, Agent, or Firm* — METIS IP LLC

(57) ABSTRACT

A method may include obtaining a first image related to one or more target objects generated by a first scan. The method may also include obtaining a first radiation therapy plan for treating the one or more target objects. The method may also include obtaining a second image related to the one or more target objects generated by a second scan. The second scan may be performed later than the first scan. The method may also include determining, based on the first radiation therapy plan, the first image, and the second image, a target radiation therapy plan to treat the one or more target objects. The target radiation therapy plan may be the first radiation therapy plan or a second radiation therapy plan associated with the second image, wherein at least a portion of the determining the target radiation therapy plan may be performed in parallel.

20 Claims, 7 Drawing Sheets

(58) Field of Classification Search
CPC ....... A61B 5/704; A61B 6/0492; A61B 5/706; A61B 6/487; A61B 6/461; A61B 6/566; A61B 6/032; A61B 6/037; A61B 6/4405; A61B 6/547; A61B 6/5217; A61B 2034/2051; A61B 2090/364; A61B 2034/2055; A61B 2090/378; A61B 6/08; A61B 5/015; A61B 8/4245; A61B 8/4209; A61B 8/4488; A61B 8/4494; A61B 8/56; A61B 8/4263; A61B 8/5207; A61B 8/483; A61B 8/08; A61B 8/4254; A61B 8/4483; A61B 8/4477; A61B 8/13; A61B 2017/320069; A61B 8/565; A61B 2565/164; A61B 2562/164; A61B 6/583; A61N 5/1049; A61N 2005/1061; A61N 5/1071; A61N 5/1038; A61N 5/1039; A61N 2005/1072; A61N 5/103; A61N 5/1069; A61N 2005/1051; A61N 2005/1063; A61N 2005/1059; A61N 5/1045; A61N 5/1031; A61N 5/1001; A61N 5/1081; A61N 5/1064; A61N 2005/1055; A61N 2005/1052; A61N 5/107; A61N 5/1067; A61N 2005/1062; A61N 2005/1056; A61N 2005/1054; A61N 5/1037; A61N 2005/1076; A61N 2005/105; A61N 7/02; A61N 7/00; A61N 2007/0078; A61N 5/1065; A61N 5/1083; A61N 5/1075; A61N 5/1043; A61N 2005/1091; G06F 19/321; G16H 20/40; G16H 30/20; G16H 50/30; G06T 7/246; G06T 7/0012; G06T 2207/30004; G03H 5/00; G03H 1/2249; G03H 1/02; G03H 2210/30; G01V 8/005; H04J 13/00
USPC .......................................................... 378/65
See application file for complete search history.

(56) References Cited

U.S. PATENT DOCUMENTS

| | | |
|---|---|---|
| 2005/0251029 A1 | 11/2005 | Khamene et al. |
| 2008/0031406 A1 | 2/2008 | Yan et al. |
| 2008/0101669 A1* | 5/2008 | Jeung .................... G01B 11/27 382/128 |
| 2015/0141733 A1 | 5/2015 | Kumar et al. |
| 2017/0014642 A1 | 1/2017 | An et al. |
| 2017/0340902 A1 | 11/2017 | Vilsmeier et al. |
| 2018/0221685 A1 | 8/2018 | Eriksson |
| 2018/0318605 A1 | 11/2018 | Da Silva Rodrigues et al. |
| 2018/0339173 A1* | 11/2018 | Kilby .................. A61N 5/1043 |
| 2019/0099619 A1 | 4/2019 | Maltz |
| 2019/0201717 A1 | 7/2019 | Shangguan et al. |
| 2019/0336793 A1 | 11/2019 | Zhou et al. |
| 2020/0038683 A1 | 2/2020 | Schadewaldt et al. |
| 2020/0206536 A1* | 7/2020 | Wang .................. A61N 5/1067 |

OTHER PUBLICATIONS

International Search Report in PCT/CN2020/079488 mailed on Nov. 30, 2020, 4 pages.
Written Opinion in PCT/CN2020/079488 mailed on Nov. 30, 2020, 5 pages.

* cited by examiner

SYSTEMS AND METHODS FOR GENERATING ADAPTIVE RADIATION THERAPY PLAN

CROSS-REFERENCE TO RELATED APPLICATIONS

This application is a continuation of International Application No. PCT/CN2020/079488 filed on Mar. 16, 2020, the contents of which are incorporated herein by reference to its entirety.

TECHNICAL FIELD

The present disclosure generally relates to systems and methods for radiation therapy, and more particularly, to systems and methods for generating an adaptive radiation therapy plan.

BACKGROUND

Radiation therapy is widely used in cancer therapy and is also indicated for several other health conditions. Conventionally, a radiation therapy plan (also referred to as treatment plan) for a cancer patient is generated before treatment starts. The radioactive rays may be delivered to the patient during several treatment fractions according to the radiation therapy plan, spread over a treatment period of multiple days. However, during the treatment period, the anatomy of the tumor or other tissues (e.g., tissue surrounding the tumor) may change. For example, the tumor may grow, deform, or shrink. If the original treatment plan is used after the change (e.g., shrinkage) of the target structure, there is a high risk to affect healthy tissue by applying a high radiation dose to such tissue. This issue can be avoided or mitigated in adaptive radiation therapy. In accordance with this approach images of the target structure are acquired during the course of the radiation therapy (e.g., between certain treatment fractions) in order to identify a change in the delineation of the target structure. Then, a re-planning procedure is carried out to adapt the treatment plan to the changed delineation of the target structure. The re-planning procedure needs to be performed rapidly; otherwise, it may lead to delays in the delivery of the radiation treatment, which can compromise the outcome of the radiation therapy, since an optimal efficacy of the therapy is achieved when it is delivered sufficiently quickly so that a repopulation of tumor cells is avoided. Therefore, it is desirable to provide systems and methods for generating an adaptive radiation therapy plan rapidly.

SUMMARY

According to a first aspect of the present disclosure, a system for generating an adaptive radiation therapy plan may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a first image related to one or more target objects generated by a first scan. The one or more processors may obtain a first radiation therapy plan for treating the one or more target objects. The first radiation therapy plan may be associated with the first image. The one or more processors may obtain a second image related to the one or more target objects generated by a second scan. The second scan may be performed later than the first scan. The one or more processors may determine, based on the first radiation therapy plan, the first image, and the second image, a target radiation therapy plan to treat the one or more target objects. The target radiation therapy plan may be the first radiation therapy plan or a second radiation therapy plan associated with the second image, wherein at least a portion of the determining the target radiation therapy plan may be performed in parallel.

In some embodiments, to determine the target radiation therapy plan, the one or more processors may generate a registration result by performing image registration between the first image and the second image. The one or more processors may determine one or more regions of interest (ROIs) in the second image based on the registration result. The one or more processors may determine an accumulated dose in the second image based on the registration result. The accumulated dose may have been delivered to the one or more target objects. The one or more processors may estimate a first dose distribution in the second image based on the first radiation therapy plan. An operation for determining the one or more ROIs in the second image based on the registration result and an operation for determining the accumulated dose in the second image based on the registration result may be performed in parallel. Alternatively or additionally, an operation for estimating the first dose distribution in the second image based on the first radiation therapy plan may be performed in parallel with at least one of an operation for generating the registration result by performing the image registration between the first image and the second image and the operation for determining the one or more ROIs in the second image based on the registration result.

In some embodiments, to determine the one or more ROIs in the second image, the one or more processors may automatically determine one or more first ROIs of the one or more ROIs in the second image. The one or more processors may receive a first instruction for modifying or accepting the one or more first ROIs that are automatically determined. The one or more processors may process at least one of the one or more first ROIs based on the first instruction. The one or more processors may automatically determine one or more second ROIs of the one or more ROIs in the second image. An operation for automatically determining the one or more second ROIs of the one or more ROIs in the second image may be performed in parallel with at least one of an operation for receiving the first instruction for modifying or accepting the one or more first ROIs that are automatically determined and an operation for processing the at least one of the one or more first ROIs based on the first instruction.

In some embodiments, to determine the one or more ROIs in the second image, the one or more processors may estimate a length of time for determining each of the one or more ROIs. The one or more processors may rank the lengths of time. The one or more processors may automatically determine the one or more ROIs based on the ranking result.

In some embodiments, to determine the one or more ROIs in the second image, the one or more processors may automatically determine a third ROI of the one or more ROIs based on a segmentation algorithm. The one or more processors may automatically determine a fourth ROI of the one or more ROIs based on a deformable registration result by performing a deformable registration between the first image and the second image. The one or more processors may automatically determine a fifth ROI of the one or more ROIs based on a rigid registration result by performing a rigid registration between the first image and the second image. At least two of an operation for automatically determining the third ROI of the one or more ROIs based on the segmentation algorithm, an operation for automatically determining the fourth ROI of the one or more ROIs based on the deformable registration result by performing the deformable registration between the first image and the second image, and an operation for automatically determining the fifth ROI of the one or more ROIs based on the rigid registration result by performing the rigid registration between the first image and the second image may be performed in parallel.

In some embodiments, to determine the target radiation therapy plan, the one or more processors may display the first dose distribution in the second image based on the one or more ROIs. The one or more processors may determine a dose volume diagram (DVH) based on the first dose distribution and the one or more ROIs. The one or more processors may display the DVH. The one or more processors may determine, based on the estimated first dose distribution or the DVH in the second image, whether to generate the second radiation therapy plan associated with the second image or continue using the first radiation therapy plan to treat the one or more target objects. The one or more processors may obtain one or more constraint conditions related to a radiation therapy to the one or more ROIs. The one or more processors may generate the second radiation therapy plan based on the one or more constraint conditions and the one or more ROIs in the second image. An operation for displaying the first dose distribution in the second image based on the one or more ROIs may be performed in parallel with at least one of an operation for estimating the DVH based on the first dose distribution and the one or more ROIs and an operation for displaying the DVH. Alternatively or additionally, an operation for determining, based on the estimated first dose distribution or the DVH in the second image, whether to generate the second radiation therapy plan associated with the second image or continue using the first radiation therapy plan to treat the one or more target objects may be performed in parallel with at least one of an operation for obtaining the one or more constraint conditions related to the radiation therapy to the one or more ROIs and an operation for generating the second radiation therapy plan based on the one or more constraint conditions and the one or more ROIs in the second image.

In some embodiments, to determine the target radiation therapy plan, the one or more processors may determine one or more ROIs in the second image. The one or more processors may generate a first intermediate plan by updating, based on the one or more determined ROIs, the first radiation therapy plan. The one or more processors may update the first intermediate plan by performing a plurality of iterations. A $t^{th}$ ($t=1, 2, 3 \ldots$) iteration of the plurality of iterations may include one or more of the following operations. The one or more processors may receive a second instruction for modifying or accepting a $t^{th}$ group of ROIs. The $t^{th}$ group of ROIs may include at least one of the one or more determined ROIs. The one or more processors may process the $t^{th}$ group of ROIs based on the second instruction. The one or more processors may generate a $(t+1)^{th}$ intermediate plan based on the $t^{th}$ intermediate plan and the processed $t^{th}$ group of ROIs. The one or more processors may designate the intermediate plan generated in a last iteration of the plurality of iterations as the second radiation therapy plan. An operation for generating the first intermediate plan by updating, based on the one or more determined ROIs, the first radiation therapy plan may be performed in parallel with at least one of an operation for receiving the instruction for modifying or accepting the first group of ROIs and an operation for processing the first group of ROIs based on the instruction for modifying or accepting the first group of ROIs. Alternatively or additionally, an operation for generating the $(t+1)^{th}$ intermediate plan based on the $t^{th}$ intermediate plan and the processed $t^{th}$ group of ROIs may be performed in parallel with at least one of an operation for receiving the instruction for modifying or accepting the $(t+1)^{th}$ group of ROIs and an operation for processing the $(t+1)^{th}$ group of ROIs based on the instruction for modifying or accepting the $(t+1)^{th}$ group of ROIs.

In some embodiments, to determine the target radiation therapy plan, the one or more processors may estimate an amount of work for manually modifying each of the one or more ROIs that are automatically determined. The one or more processors may assign the one or more ROIs into a plurality of groups based on the amounts of work for manually modifying the one or more ROIs. The one or more processors may generate an instruction that prompts a user to modify, based on the group assignments, the one or more ROIs.

In some embodiments, the instruction may prompt the user to batch process ROIs of the one or more ROIs that are assigned to a same group.

In some embodiments, at least one of an operation for obtaining the first image and an operation for obtaining the first radiation therapy plan may be performed during the second scan.

According to another aspect of the present disclosure, a method for generating an adaptive radiation therapy plan may include one or more of the following operations. One or more processors may obtain a first image related to one or more target objects generated by a first scan. The one or more processors may obtain a first radiation therapy plan for treating the one or more target objects. The first radiation therapy plan may be associated with the first image. The one or more processors may obtain a second image related to the one or more target objects generated by a second scan. The second scan may be performed later than the first scan. The one or more processors may determine, based on the first radiation therapy plan, the first image, and the second image, a target radiation therapy plan to treat the one or more target objects. The target radiation therapy plan may be the first radiation therapy plan or a second radiation therapy plan associated with the second image, wherein at least a portion of the determining the target radiation therapy plan may be performed in parallel.

According to yet another aspect of the present disclosure, a system for generating an adaptive radiation therapy plan may include an obtaining module configured to obtain a first image related to one or more target objects generated by a first scan. The obtaining module may be also configured to obtain a first radiation therapy plan for treating the one or more target objects. The first radiation therapy plan may be associated with the first image. The obtaining module may be also configured to obtain a second image related to the one or more target objects generated by a second scan. The second scan may be performed later than the first scan. The system may also include a plan determination module configured to determine, based on the first radiation therapy plan, the first image, and the second image, a target radiation therapy plan to treat the one or more target objects. The target radiation therapy plan may be the first radiation therapy plan or a second radiation therapy plan associated with the second image, wherein at least a portion of the determining the target radiation therapy plan may be performed in parallel.

According to yet another aspect of the present disclosure, a non-transitory computer readable medium may comprise at least one set of instructions. The at least one set of instructions may be executed by one or more processors of a computing device. The one or more processors may obtain a first image related to one or more target objects generated by a first scan. The one or more processors may obtain a first radiation therapy plan for treating the one or more target objects. The first radiation therapy plan may be associated with the first image. The one or more processors may obtain a second image related to the one or more target objects generated by a second scan. The second scan may be performed later than the first scan. The one or more processors may determine, based on the first radiation therapy plan, the first image, and the second image, a target radiation therapy plan to treat the one or more target objects. The target radiation therapy plan may be the first radiation therapy plan or a second radiation therapy plan associated with the second image, wherein at least a portion of the determining the target radiation therapy plan may be performed in parallel.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "module," and/or "block" used herein are one method to distinguish different components, elements, parts, section or assembly of different level in ascending order. However, the terms may be displaced by another expression if they achieve the same purpose.

Figure 2:
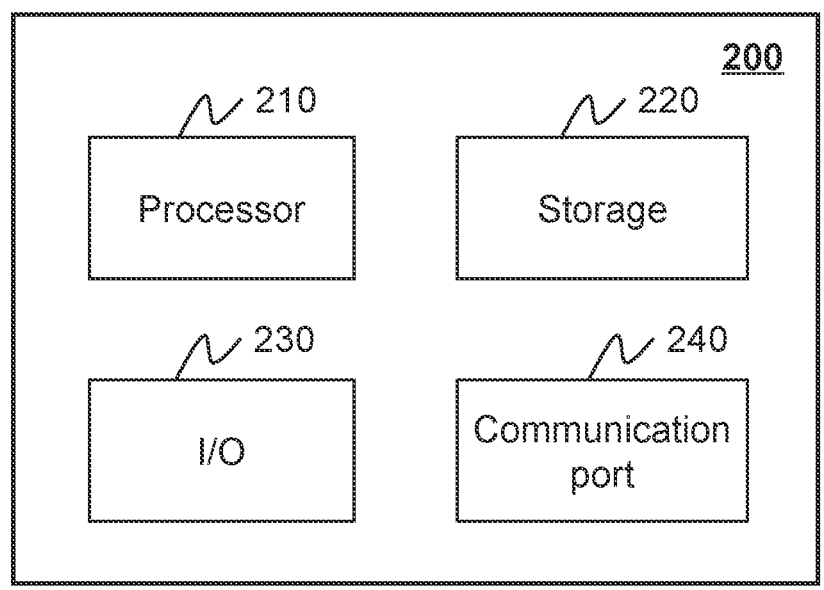
FIG. 2 is a schematic diagram illustrating hardware and/or software components of an exemplary computing device according to some embodiments of the present disclosure.

Generally, the word "module," or "block," as used herein, refers to logic embodied in hardware or firmware, or to a collection of software instructions. A module, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Electrically Programmable Read-Only-Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a module or block is referred to as being "connected to," or "coupled to," another module, or block, it may be directly connected or coupled to, or communicate with the other module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system, an X-ray system, a computed tomography (CT) system, a positron emission computed tomography (PET) system, an ultrasonic system, or the like, or any combination thereof. The multi-modality imaging system may include, for example, a computed tomography-magnetic resonance imaging (CT-MRI) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, a positron emission tomography-computed tomography (PET-CT) etc. In some embodiments, the medical system may include a treatment system. The treatment system may include a treatment plan system (TPS), image-guide radiotherapy (IGRT), etc. The image-guide radiotherapy (IGRT) may include a treatment device and an imaging device. The treatment device may include a linear accelerator, a cyclotron, a synchrotron, etc., configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

For brevity, an image, or a portion thereof (e.g., an ROI in the image) corresponding to an object (e.g., a tissue, an organ, a tumor, etc., of a subject (e.g., a patient, etc.)) may be referred to as an image, or a portion of thereof (e.g., an ROI) of or including the object, or the object itself. For instance, an ROI corresponding to the image of a tumor may be described as that the ROI includes a tumor. As another example, an image of or including a liver may be referred to a liver image, or simply liver. For brevity, that a portion of an image corresponding to an object is processed (e.g., extracted, segmented, etc.) may be described as the object is processed. For instance, a portion of an image corresponding to a tumor is extracted from the rest of the image may be described as that the tumor is extracted.

Provided herein are systems and methods for generating an adaptive radiation therapy plan during a radiation therapy/treatment. When performing the re-planning process in the adaptive radiation therapy, the systems and/or methods may perform at least two operations of the re-planning process in parallel, thereby improving the efficiency of the generation of the adaptive radiation therapy plan.

Figure 1:
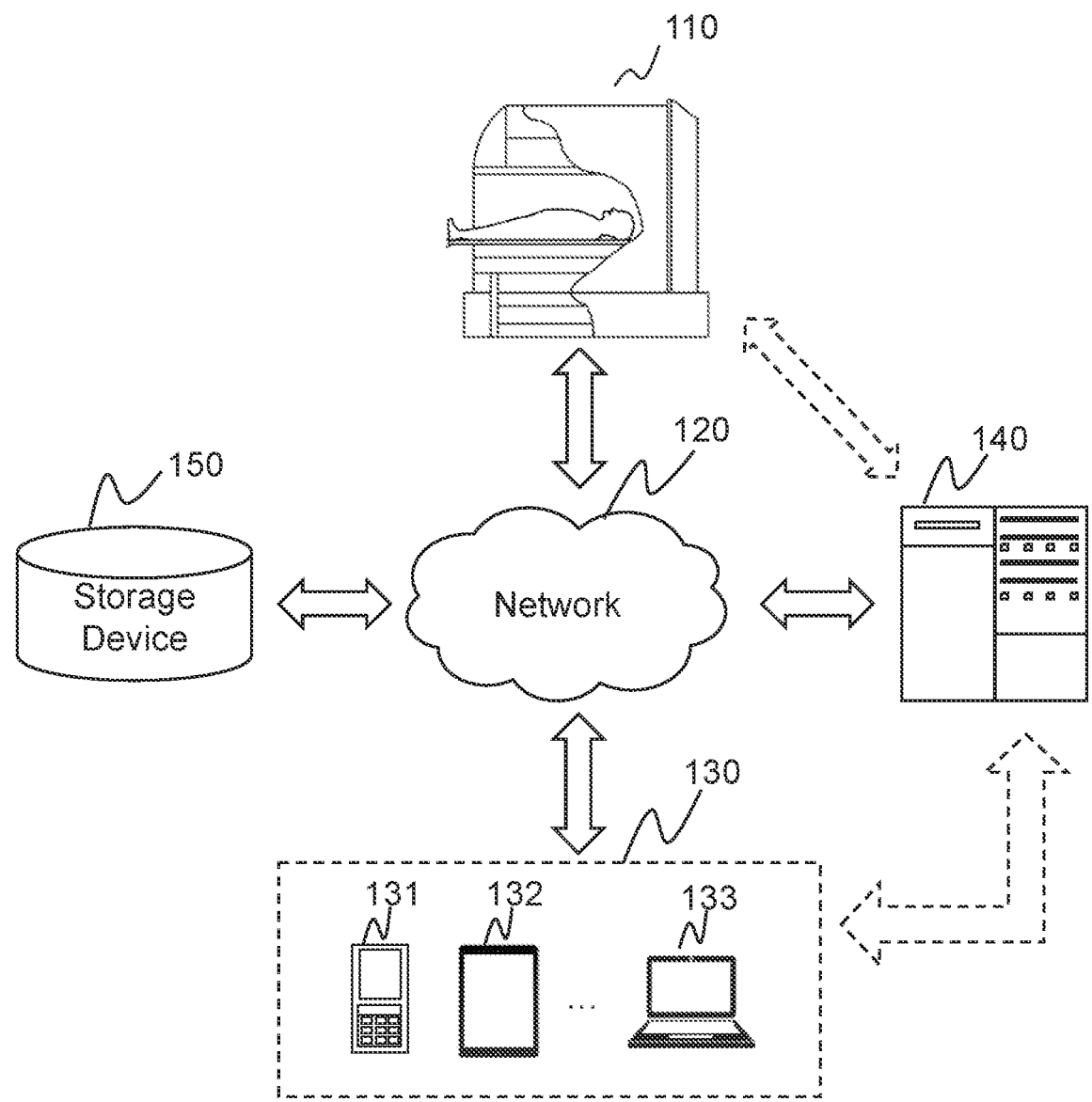
FIG. 1 is a schematic diagram illustrating an exemplary radiation therapy system according to some embodiments of the present disclosure.

FIG. 1 is a schematic diagram illustrating an exemplary radiation therapy system 100 according to some embodiments of the present disclosure. As shown in FIG. 1, the radiation therapy system 100 may include a radiation device 110, a network 120, one or more terminals 130, a processing device 140, and a storage device 150.

Radiation therapy, is therapy using ionizing radiation, generally as part of cancer treatment to control or kill malignant cells. Radiation therapy may be delivered by a linear accelerator (e.g., the radiation device 110 in the radiation therapy system 100 in FIG. 1). The radiation therapy may include an external radiation therapy, a Brachytherapy, an intraoperative radiotherapy, a radioisotope therapy, a deep inspiration breath-hold (DIBH), etc. The external beam radiation therapy may include a conventional external beam radiation therapy (2DXRT), a stereotactic radiation therapy (e.g., a stereotactic radiosurgery, a stereotactic body radiation therapy, etc.), a virtual simulation and three-dimensional conformal radiation therapy (3DCRT), an intensity-modulated radiation therapy (IMRT), a volumetric modulated arc therapy (VMAT), a particle therapy, an Auger therapy (AT), etc.

The radiation device 110 may emit radioactive rays to a subject (e.g., a patient) to perform a treatment to control or kill malignant cells. The radioactive rays may include α rays, β rays, γ rays, X rays, neutrons, etc. The radiation device 110 may include a medical linear accelerator, a Cobalt-60 device, a Gamma knife, X knife, a proton accelerator, a brachytherapy device, or the like, or any combination thereof. In some embodiments, before treatment (or a portion of the treatment), an imaging scan may be performed to identify the tumor and surrounding normal structures of the subject. Accordingly, the radiation therapy system 100 may further include an imaging device (not shown in FIG. 1) such as an X-ray device, a computed tomography (CT) device, a positron emission computed tomography (PET) device, a magnetic resonance imaging (MRI) device, or the like, or any combination thereof.

In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

For convenience, the description of the methods and/or systems for generating an adaptive radiation therapy plan in this disclosure is provided in connection with a radiation therapy/treatment. It should be noted that the description of the methods and/or systems for generating an adaptive radiation therapy plan applied in the radiation therapy is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

The network 120 may include any suitable network that can facilitate exchange of information and/or data for the radiation therapy system 100. In some embodiments, one or more components of the radiation therapy system 100 (e.g., the radiation device 110, the terminal 130, the processing device 140, the storage device 150, etc.) may communicate information and/or data with one or more other components of the radiation therapy system 100 via the network 120. For example, the processing device 140 may obtain information related to a radiation therapy plan or images from the radiation device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation therapy system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the radiation device 110, the terminal 130, and/or the storage device 150. For example, the processing device 140 may generate and update a radiation therapy plan. In some embodiments, the processing device 140 may be a single server or a server group. The server group may be centralized or distributed. In some embodiments, the processing device 140 may be local or remote. For example, the processing device 140 may access information and/or data stored in the radiation device 110, the terminal 130, and/or the storage device 150 via the network 120. As another example, the processing device 140 may be directly connected to the radiation device 110, the terminal 130 and/or the storage device 150. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the radiation device 110, the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiation therapy system 100 (e.g., the processing device 140, the terminal 130, etc.). One or more components in the radiation therapy system 100 may access the data or instructions stored in the storage device 150 via the network 120. In some embodiments, the storage device 150 may be directly connected to or communicate with one or more other components in the radiation therapy system 100 (e.g., the processing device 140, the terminal 130, etc.). In some embodiments, the storage device 150 may be part of the processing device 140. In some embodiments, the processing device 140 may be connected to or communicate with the radiation device 110 via the network 120, or at the backend of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein.

The computer instructions may include, for example, routines, programs, objects, components, data structures, procedures, modules, and functions, which perform particular functions described herein. For example, the processor 210 may process image data obtained from the radiation device 110, the terminal 130, the storage device 150, and/or any other component of the radiation therapy system 100. In some embodiments, the processor 210 may process the image(s) based on information relating to a treatment plan. In some embodiments, the processor 210 may update a radiation therapy plan related to the subject. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step X and step Y, it should be understood that step X and step Y may also be performed by two or more different processors jointly or separately in the computing device 200 (e.g., a first processor executes step X and a second processor executes step Y, or the first and second processors jointly execute steps X and Y).

The storage 220 may store data/information obtained from the radiation device 110, the terminal 130, the storage device 150, and/or any other component of the radiation therapy system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for generating and updating an adaptive radiation therapy plan.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with digital imaging and communications in medicine (DICOM) protocol.

Figure 3:
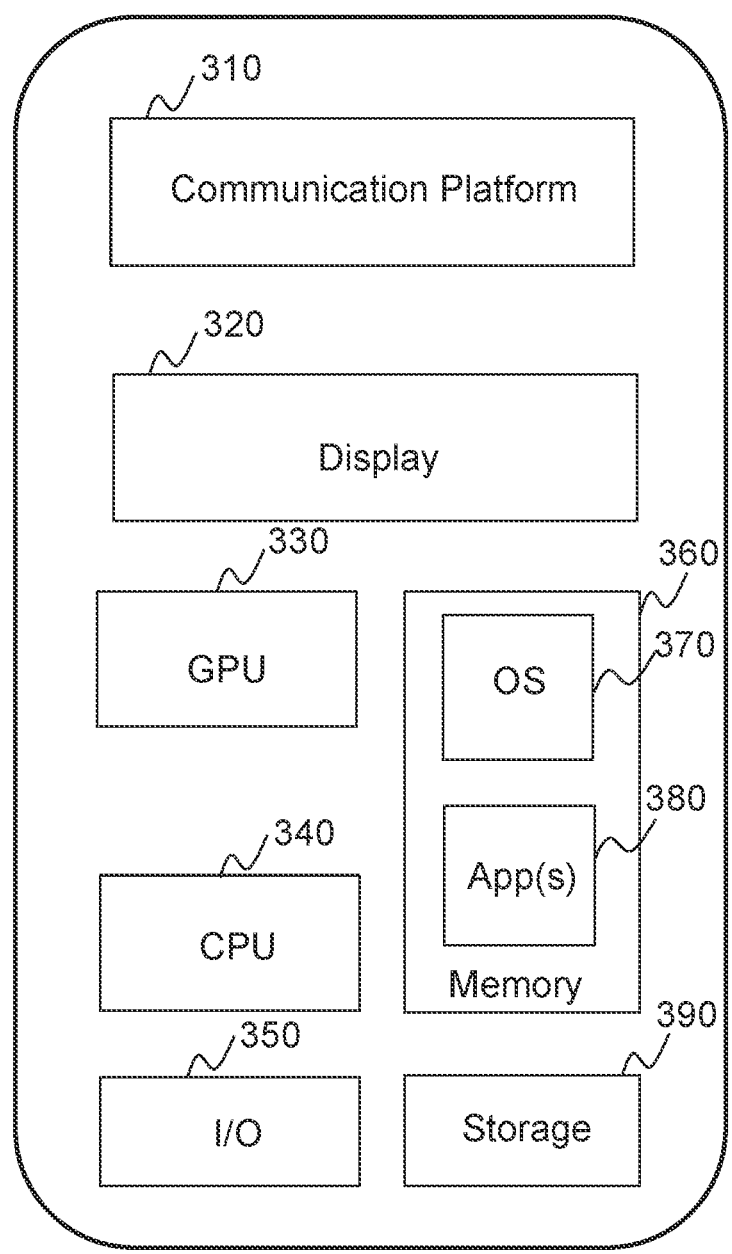
FIG. 3 is a schematic diagram illustrating hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation therapy system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
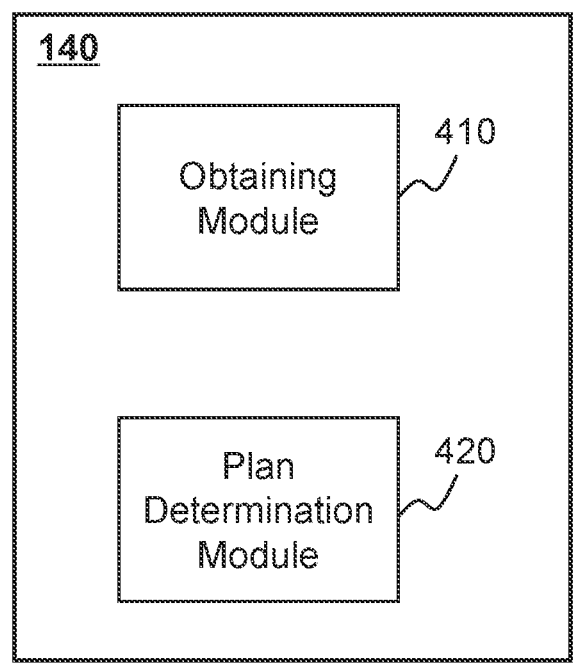
FIG. 4 is a block diagram illustrating an exemplary processing device according to some embodiments of the present disclosure.

FIG. 4 is a schematic block diagram illustrating an exemplary processing device according to some embodiments of the present disclosure. The processing device 140 may include an obtaining module 410 and a plan determination module 420.

The obtaining module 410 may be configured to obtain a first image related to a target object generated by a first scan.

The obtaining module 410 may be further configured to obtain a first radiation therapy plan for treating the target object. The first radiation therapy plan may be associated with the first image. In the present disclosure, "treatment plan" and "radiation therapy plan" are used interchangeably.

In some embodiments, before the whole treatment starts, one or more imaging scans (e.g., the first scan) may be performed to identify the target structure (e.g., tumor) and surrounding normal structures of the target object and one or more images (e.g., the first image) may be generated based on the one or more imaging scans.

In some embodiments, the first scan may be performed by scanning the target object via the imaging device in the radiation therapy system 100. For example, the imaging device may be a CT imaging device as described in connection with FIG. 1.

The first image may be generated based on image data acquired from the first scan. One or more components in the radiation therapy system 100 (e.g., the processing device 140) may process the image data to provide the first image. The first image may include one or more medical images such as an MRI image, a CT image, a PET image, an ultrasonic image, an X-ray image, or the like, or any combination thereof. The first image and/or the corresponding image data may be stored in a storage medium (e.g., the storage device 150 and/or the storage 220). The processing device 140 (e.g., the obtaining module 410) may access the storage medium to obtain the first image.

The first image may indicate information related to the target object, such as the delineation, morphology, condition of the target structure (e.g., tumor) and/or the surrounding tissue, or the like, or any combination thereof. In some embodiments, the first image may be two-dimensional (2D) or three-dimensional (3D).

A treatment plan may be generated based on the one or more images. The treatment plan may describe how to perform a radiation therapy on a patient, or more specifically, how radioactive rays are delivered to a region of interest (ROI) of a patient during a course of treatment lasting days or weeks or months.

In some embodiments, since it may be unbearable for a patient to subject to the total dose prescribed by the treatment plan in one treatment session, the whole treatment may be divided into a plurality of treatment fractions. The patient may receive a portion of the total radiation dose in each one of the plurality of treatment fractions (e.g., one or two treatment fractions a day).

The treatment parameters corresponding to each treatment fraction for radiation delivery and/or controlling the radiation device 110 may be defined in the treatment plan, such as a planned fraction duration, a planned radiation dose, a planned radiation delivery direction, a planned radiation beam shape, a planned radiation beam cross-sectional area, a planned ROI of the target object, or the like, or any combination thereof.

In some embodiments, the first radiation therapy plan may be part of the original treatment plan that includes the treatment parameters corresponding to a treatment fraction to be delivered. For example, the whole treatment may be divided into 4 treatment fractions, such as, in turn, fractions A-D. The patient has received fractions A and B. The first radiation therapy plan may be part of the original treatment plan for a treatment fraction (e.g., fraction C) subsequent to the fraction(s) that have been performed (e.g., fractions A and B).

The obtaining module 410 may be further configured to obtain a second image related to the target object generated by a second scan. The second scan may be performed later than the first scan.

During the treatment period, the anatomy of the target structure (e.g., tumor) or other tissues (e.g., tissue surrounding the tumor) of the target object may change. For example, the tumor may grow, deform, or shrink. If the original treatment plan is used after the change (e.g., shrinkage) of the target structure, there is a risk to affect healthy tissue from a radiation dose applied to such tissue. In adaptive radiation therapy, an inter-fraction plan adaptation may be performed. For instance, one or more images (e.g., the second image) of the target structure may be acquired during the course of the radiation therapy (e.g., between certain treatment fractions) in order to determine the changed delineation of the target structure to adapt the treatment plan to the changed delineation of the target structure.

The second scan may be performed before a treatment fraction (not the first treatment fraction of the whole treatment) is performed on the target object. For example, the whole treatment may be divided into 4 treatment fractions, such as, in turn, fractions A-D. The patient has received fractions A and B. The second scan may be performed before fraction C is delivered to the patient.

In some embodiments, the second scan may be performed by scanning the target object via the imaging device in the radiation therapy system 100. For example, the imaging device may be a CT imaging device as described in connection with FIG. 1.

The second image may be generated based on image data acquired from the second scan. One or more components in the radiation therapy system 100 (e.g., the processing device 140) may process the image data to provide the second image. The second image may include one or more medical images such as an MRI image, a CT image, a PET image, an ultrasonic image, an X-ray image, or the like, or any combination thereof. The second image and/or the corresponding image data may be stored in a storage medium (e.g., the storage device 150 and/or the storage 220). The processing device 140 (e.g., the obtaining module 410) may access the storage medium to obtain the second image.

The second image may indicate information related to the target object, such as the delineation, morphology, condition of the target structure (e.g., tumor) and/or the surrounding tissue, or the like, or any combination thereof. In some embodiments, the second image may be two-dimensional (2D) or three-dimensional (3D).

The plan determination module 420 may be configured to determine a target radiation therapy plan based on the first radiation therapy plan, the first image, and the second image to treat the target object. The target radiation therapy plan may be the first radiation therapy plan from the original treatment plan or a second radiation therapy plan associated with the second image. In some embodiments, the target radiation therapy plan may correspond to the treatment fraction to be delivered to the target object. For example, the whole treatment may be divided into 4 treatment fractions, such as, in turn, fractions A-D. The patient has received fractions A and B. In fraction C, radioactive rays may be delivered to the patient according to the target radiation therapy plan.

The second radiation therapy plan may be obtained by updating the first radiation therapy plan based on the second image to adapt the original treatment plan to the changed delineation of the target structure in the second image after one or more treatment fractions.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided into two or more units. For example, the obtaining module 410 may be divided into two units. One of the two unit may be configured to obtain the first image and the second image, and the other one of the two unit may be configured to obtain the first radiation therapy plan.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of the components of the processing device 140 may include a storage device. Additionally or alternatively, the components of the processing device 140 may share a common storage device.

Figure 5:
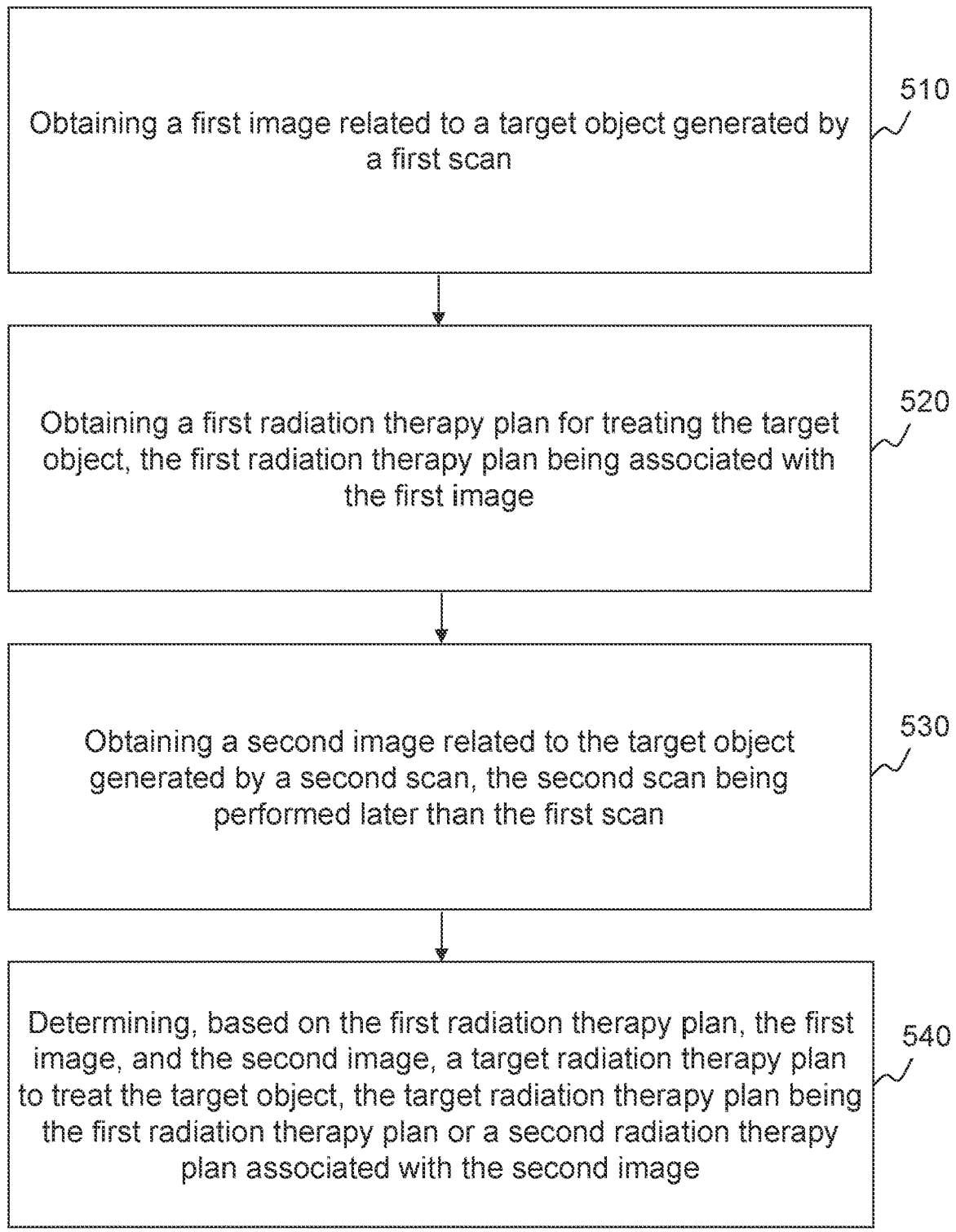
FIG. 5 is a flowchart illustrating an exemplary process for determining a target radiation therapy plan according to some embodiments of the present disclosure.

FIG. 5 is a flowchart illustrating an exemplary process for determining a target radiation therapy plan according to some embodiments of the present disclosure. In some embodiments, at least part of process 500 may be performed by the processing device 140 (implemented in, for example, the computing device 200 shown in FIG. 2). For example, the process 500 may be stored in a storage device (e.g., the storage device 150 and/or the storage 220) in the form of instructions (e.g., an application), and invoked and/or executed by the processing device 140 (e.g., the processor 210 illustrated in FIG. 2 and/or or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

For brevity, in the description of the process, an adaptive radiation therapy for treating a target object may be taken as an example. It should be noted that the adaptive radiation therapy for treating a target object described below is provided for illustration purposes and not intended to be limiting. For persons having ordinary skills in the art, the process 500 may be applied to other similar situations, such as an adaptive radiation therapy for treating more than one target object.

In some embodiments, the processing device 140 may perform the process 500 (e.g., a re-planning process) before a treatment fraction (not the first treatment fraction of a whole treatment) is delivered. The processing device 140 may perform the process 500 online or offline.

In 510, the processing device 140 (e.g., the obtaining module 410) may obtain a first image related to a target object generated by a first scan.

In 520, the processing device 140 (e.g., the obtaining module 410) may obtain a first radiation therapy plan for treating the target object. The first radiation therapy plan may be associated with the first image. In the present disclosure, "treatment plan" and "radiation therapy plan" are used interchangeably.

In some embodiments, before the whole treatment starts, one or more imaging scans (e.g., the first scan) may be performed to identify the target structure (e.g., tumor) and surrounding normal structures of the target object and one or more images (e.g., the first image) may be generated based on the one or more imaging scans.

In some embodiments, the first scan may be performed by scanning the target object via the imaging device in the radiation therapy system 100. For example, the imaging device may be a CT imaging device as described in connection with FIG. 1.

The first image may be generated based on image data acquired from the first scan. One or more components in the radiation therapy system 100 (e.g., the processing device 140) may process the image data to provide the first image. The first image may include one or more medical images such as an MRI image, a CT image, a PET image, an ultrasonic image, an X-ray image, or the like, or any combination thereof. The first image and/or the corresponding image data may be stored in a storage medium (e.g., the storage device 150 and/or the storage 220). The processing device 140 (e.g., the obtaining module 410) may access the storage medium to obtain the first image.

The first image may indicate information related to the target object, such as the delineation, morphology, condition of the target structure (e.g., tumor) and/or the surrounding tissue, or the like, or any combination thereof. In some embodiments, the first image may be two-dimensional (2D) or three-dimensional (3D).

A treatment plan may be generated based on the one or more images. The treatment plan may describe how to perform a radiation therapy on a patient, or more specifically, how radioactive rays are delivered to a region of interest (ROI) of a patient during a course of treatment lasting days or weeks or months.

In some embodiments, since it may be unbearable for a patient to subject to the total dose prescribed by the treatment plan in one treatment session, the whole treatment may be divided into a plurality of treatment fractions. The patient may receive a portion of the total radiation dose in each one of the plurality of treatment fractions (e.g., one or two treatment fractions a day).

The treatment parameters corresponding to each treatment fraction for radiation delivery and/or controlling the radiation device 110 may be defined in the treatment plan, such as a planned fraction duration, a planned radiation dose, a planned radiation delivery direction, a planned radiation beam shape, a planned radiation beam cross-sectional area, a planned ROI of the target object, or the like, or any combination thereof.

In some embodiments, the first radiation therapy plan may be part of the original treatment plan that includes the treatment parameters corresponding to a treatment fraction to be delivered. For example, the whole treatment may be divided into 4 treatment fractions, such as, in turn, fractions A-D. The patient has received fractions A and B. The first radiation therapy plan may be part of the original treatment plan for a treatment fraction (e.g., fraction C) subsequent to the fraction(s) that have been performed (e.g., fractions A and B).

In 530, the processing device 140 (e.g., the obtaining module 410) may obtain a second image related to the target object generated by a second scan. The second scan may be performed later than the first scan.

During the treatment period, the anatomy of the target structure (e.g., tumor) or other tissues (e.g., tissue surrounding the tumor) of the target object may change. For example, the tumor may grow, deform, or shrink. If the original treatment plan is used after the change (e.g., shrinkage) of the target structure, there is a risk to affect healthy tissue from a radiation dose applied to such tissue. In adaptive radiation therapy, an inter-fraction plan adaptation may be performed. For instance, one or more images (e.g., the second image) of the target structure may be acquired during the course of the radiation therapy (e.g., between certain treatment fractions) in order to determine the changed delineation of the target structure to adapt the treatment plan to the changed delineation of the target structure.

The second scan may be performed before a treatment fraction (not the first treatment fraction of the whole treatment) is performed on the target object. For example, the whole treatment may be divided into 4 treatment fractions, such as, in turn, fractions A-D. The patient has received fractions A and B. The second scan may be performed before fraction C is delivered to the patient.

In some embodiments, the second scan may be performed by scanning the target object via the imaging device in the radiation therapy system 100. For example, the imaging device may be a CT imaging device as described in connection with FIG. 1.

The second image may be generated based on image data acquired from the second scan. One or more components in the radiation therapy system 100 (e.g., the processing device 140) may process the image data to provide the second image. The second image may include one or more medical images such as an MRI image, a CT image, a PET image, an ultrasonic image, an X-ray image, or the like, or any combination thereof. The second image and/or the corresponding image data may be stored in a storage medium (e.g., the storage device 150 and/or the storage 220). The processing device 140 (e.g., the obtaining module 410) may access the storage medium to obtain the second image.

The second image may indicate information related to the target object, such as the delineation, morphology, condition of the target structure (e.g., tumor) and/or the surrounding tissue, or the like, or any combination thereof. In some embodiments, the second image may be two-dimensional (2D) or three-dimensional (3D).

In 540, the processing device 140 (e.g., the plan determination module 420) may determine a target radiation therapy plan based on the first radiation therapy plan, the first image, and the second image to treat the target object. The target radiation therapy plan may be the first radiation therapy plan from the original treatment plan or a second radiation therapy plan associated with the second image. In some embodiments, the target radiation therapy plan may correspond to the treatment fraction to be delivered to the target object. For example, the whole treatment may be divided into 4 treatment fractions, such as, in turn, fractions A-D. The patient has received fractions A and B. In fraction C, radioactive rays may be delivered to the patient according to the target radiation therapy plan.

The second radiation therapy plan may be obtained by updating the first radiation therapy plan based on the second image to adapt the original treatment plan to the changed delineation of the target structure in the second image after one or more treatment fractions.

The re-planning procedure needs to be performed rapidly; otherwise, it may lead to delays in the delivery of the radiation treatment, which can compromise the outcome of the radiation therapy, since an optimal efficacy of the therapy is achieved when it is delivered sufficiently quickly so that a repopulation of tumor cells is avoided or reduced. In some embodiments, the processing device 140 may perform a plurality of operations to perform the re-planning procedure. In order to achieve the above purposes, the processing device 140 may perform at least two of the plurality of operations that are independent of each other in parallel. As used herein, a parallel performance of two or more operations indicates that at least a portion of the two or more operations are performed simultaneously, even if the performance of the two or more operations may start or be finished at a same time or at different times. Merely by way of example, the processing device 140 may be regarded as implementing at least two independent threads that proceed in parallel each of which performs one or more operations in the adaptive radiation therapy. For example, during the process for determining the target radiation therapy plan, a first operation for determining one or more ROIs in the second image and a second operation for estimating a first dose distribution related to the first radiation therapy plan may be performed. The first operation and the second operation are independent of each other. The processing device 140 may perform the first operation and the second operation in parallel. For example, the processing device 140 may perform initiate the second operation when the first operation is being performed, instead of initiating the second operation after the first operation is completed.

Figure 6:
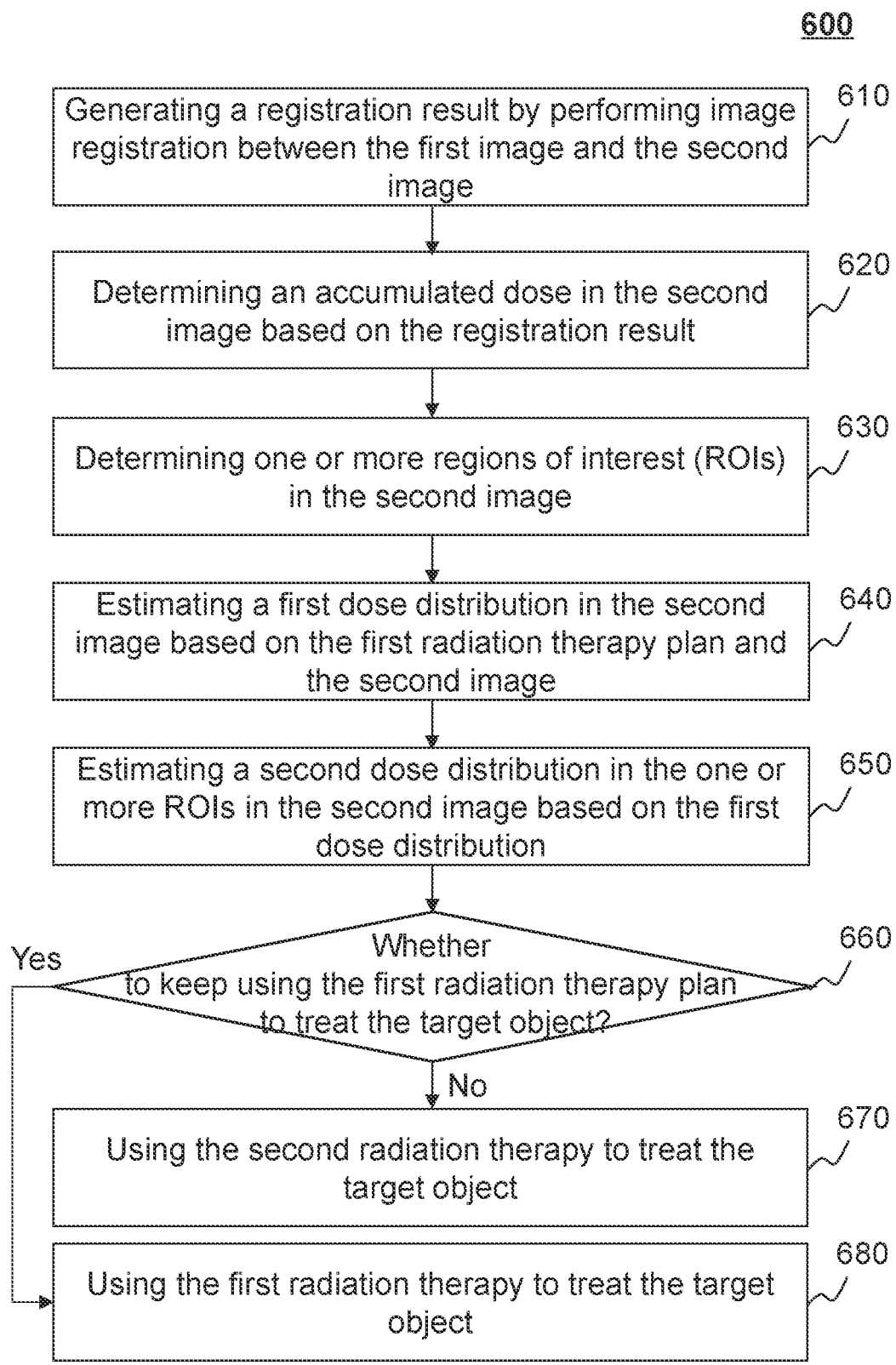
FIG. 6 is a flowchart illustrating an exemplary process for determining a target radiation therapy plan according to some embodiments of the present disclosure.
Figure 7:
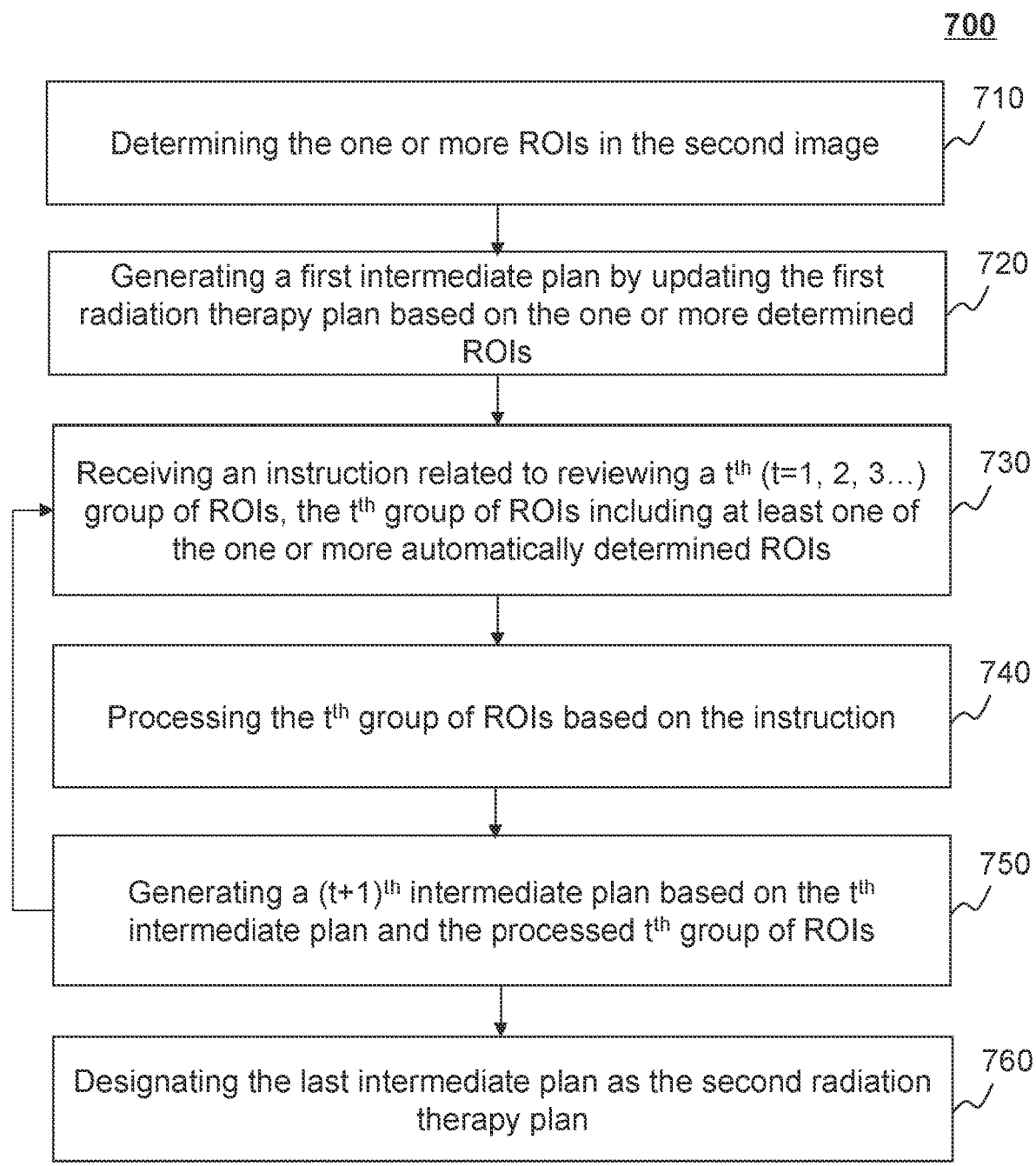
FIG. 7 is a flowchart illustrating an exemplary process for determining a target radiation therapy plan according to some embodiments of the present disclosure.

More descriptions of the determination of the target radiation therapy plan may be found elsewhere in the present disclosure (e.g., FIGS. 6-7, and the descriptions thereof).

In some embodiments, shortly after (e.g., within minutes, within hours, on the same day, etc.) acquiring the second image based on the second scan, the processing device 140 may perform operation 540. In this case, the first image and the first radiation therapy plan may be obtained during the second scan. In some embodiments, after acquiring the second image based on the second scan, the processing device 140 may perform operation 540 at a defined time, e.g., on the second day, in a few days, etc.

In some embodiments, shortly after (e.g., within minutes, within hours, on the same day, etc.) performing the process 500 of the re-planning process, the processing device 140 may cause a treatment fraction to be delivered to the target object based on the target radiation therapy plan (e.g., control the radiation device 110 to deliver a treatment fraction based on the target radiation therapy plan). In some embodiments, after performing the process 500 of the re-planning process, the processing device 140 may cause a treatment fraction to be delivered to the target object based on the target radiation therapy plan (e.g., control the radiation device 110 to deliver a treatment fraction based on the target radiation therapy plan) at a defined time, e.g., on the second day, in a few days, etc.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 6 is a flowchart illustrating an exemplary process for determining a target radiation therapy plan according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150 and/or the storage 220) in the form of instructions (e.g., an application), and invoked and/or executed by the processing device 140 (e.g., the processor 210 illustrated in FIG. 2 and/or or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, operation 540 of process 500 may be performed based on the process 600.

In 610, the processing device 140 (e.g., the plan determination module 420) may generate a registration result by performing image registration between the first image and the second image. As used herein, image registration is a process of transforming the spatial information of different images (e.g., the first image and the second image) into a same coordinate system in order to, e.g., compare or integrate the data obtained from the different images.

The image registration may be performed based on any suitable image registration techniques including, for example, a voxel-based registration technique, a landmark-based registration technique, a segmentation-based registration technique, or the like, or a combination thereof. In some embodiments, the registration may be a rigid registration. In some embodiments, the registration may be a non-rigid deformable registration.

Merely by way of example, the second image may be registered with the first image based on the landmark-based registration technique. The landmark for registration may be a visible anatomical point that can be identified and located in an image (e.g., the first image, the second image). For example, the landmark may be a bone. In the registration, a landmark in the first image may be aligned with a corresponding landmark in the second image. The image registration of the second image with the first image may be performed to remove at least part of an error due to, for example, the misalignment of the target object when the second image is obtained compared to when the first image is obtained. The misalignment may be caused by, for example, a weight change of the target object, an error in the setup of the target object for the second scan from which the second image is obtained, or the like, or a combination thereof.

The registration result may include one or more images generated by image registration and/or a registration matrix representing a transformation relationship between the first image and the second image. For example, if a pixel of an ROI in the first image has a pair of coordinates $(x_A, y_A)$ related to a coordinate system A and a corresponding pixel in the second image has a pair of coordinates $(x_B, y_B)$ related to a coordinate system B, the processing device 140 may transform $(x_A, y_A)$ into the coordinate system B or transform $(x_B, y_B)$ into the coordinate system A using the registration matrix.

In some embodiments, the processing device 140 may automatically perform the image registration. In some embodiments, the registration result may need to be accepted by a user (e.g., a doctor, a clinician, etc.) before being used in subsequent operations, for example, determining ROIs in the second image. In some embodiments, the registration result including a fused image may be presented to the user. The fused image may be generated by fusing a registered second image and the first image using an image fusion technique. Exemplary image fusion techniques may include data-level fusion, feature-level fusion, and decision-making-level fusion. Herein, the data-level fusion may include a spatial domain algorithm, a transform domain algorithm, etc. The transform domain algorithm may include a pyramid decomposition fusion algorithm, a wavelet transform algorithm, etc. The feature-level fusion may include infrared image fusion based on heat, visible light image fusion based on brightness, etc. The decision-level fusion may be based on a Bayesian algorithm, Dempster-Shafter (DS) evidential reasoning, a voting algorithm, etc.

The user may review or analyze the registration result by accepting the registration result or modifying the registration result. User interactions with the registration result may be achieved via the I/O 230 and/or the I/O 350 and provided to the processing device 140 and/or other components of the radiation therapy system 100 via the network 120.

In 620, the processing device 140 (e.g., the plan determination module 420) may determine a distribution of an accumulated dose in the second image based on the registration result. A distribution of an accumulated dose in the second image may be a distribution of an accumulated dose of radiation that has been delivered to or received by the target object in the target structure (e.g., tumor) and surrounding normal structure after one or more treatment fractions that have been performed on the target object. In some embodiments, the distribution of an accumulated dose may be represented by an accumulated dose of each pixel/voxel in the second image. In some embodiments, the accumulated dose of each pixel/voxel in the second image may be represented as pixel or voxel values of the pixels/voxels in the second image.

In some embodiments, the distribution of the accumulated dose in the second image may be determined based on the treatment parameters corresponding to the performed treatment fractions and the registered second image. For example, the plan determination module 420 may determine the distribution of the accumulated dose in the second image by adding each dose distribution of all performed treatment fractions together. A dose distribution may reflect the radiation absorption rate related to one or more positions of the target object during the treatment fraction. The dose distribution may be represented as $\{(A1, B1), (A2, B2), \ldots (Ai, Bi), \ldots (An, Bn)\}$, where Ai may denote a position of the target object and Bi may denote the radiation dose absorbed by the position Ai of the target object. For example, the plan determination module 420 may retrieve position information of Ai (e.g., represented by the coordinates of a pixel/voxel) of the target object from the second image, and obtain information regarding a beam field applied to the position Ai based on one or more treatment parameters (e.g., the radiation beam direction and/or the radiation beam shape), and determine or estimate the radiation dose delivered to or absorbed by the position Ai based on the field dose of the plurality of treatment parameters.

In 630, the processing device 140 (e.g., the plan determination module 420) may determine one or more ROIs in the second image. The ROI may be a region of the target object in the second image including at least part of malignant tissue (e.g., a tumor, a cancer-ridden organ, or a non-cancerous target of radiation therapy). Additionally or alternatively, the ROI may include other tissue, such as normal tissue surrounding the malignant tissue.

In some embodiments, during the treatment period, the anatomy of the tumor or other tissues (e.g., tissue surrounding the tumor) may change. For example, the tumor may grow, deform, or shrink. The one or more ROIs may be determined in the second image in order to determine the changed delineation of the target structure and/or the surrounding normal structure.

In some embodiments, the one or more ROIs in the second image may be determined by performing automatic contouring and/or segmentation in the second image. For example, the automatic contouring in the second image may be performed using a machine learning model trained to identify contours of one or more ROIs. As another example, the automatic contouring and/or segmentation in the second image may be performed using an automatic contouring algorithm and/or segmentation algorithm. In some embodiments, the determination of the ROIs by performing automatic contouring and/or segmentation may be performed in parallel with operation 610.

In some embodiments, the one or more ROIs in the second image may be automatically determined based on the registration result and the first image. The plan determination module 420 may apply one or more corresponding ROIs in the first image to the registered second image and automatically determine the one or more ROIs in the second image. The one or more corresponding ROIs in the first image may be automatically determined based on, for example, a contouring algorithm and/or segmentation algorithm, or manually determined by a user of the radiation therapy system 100.

In some embodiments, the one or more automatically determined ROIs in the second image may need to be reviewed or analyzed by the user before being used. Merely by way of example, the plan determination module 420 may automatically determine the one or more ROIs in the second image using a machine learning model or an automatic contouring algorithm. The plan determination module 420 may further cause the one or more automatically determined ROIs to be presented for the user to allow the user to provide an instruction. In some embodiments, the user may provide an instruction to indicate that one or more of the at least one of the automatically determined ROIs need to be modified or are acceptable. The plan determination module 420 may keep an automatically determined ROI in the second image based on a user instruction that the ROI is acceptable (or referred to as an acceptance instruction for brevity). The plan determination module 420 may update an automatically determined ROIs in the second image based on a user instruction that the ROI needs to be modified (or referred to as a modification instruction for brevity). The user may provide an instruction via a user interface implemented on, e.g., the I/O 350 of a terminal 130, and/or the I/O 230 of the processing device 140.

In some embodiments, the one or more ROIs in the second image may be determined manually by a user (e.g., a doctor, a clinician, etc.) through, for example, the I/O 230 of the processing device 140 and/or the I/O 350 of the one or more terminals 130. Merely by way of example, a clinician may directly draw the one or more ROIs in the second image on a touch screen or using a mouse. In some embodiments, the manual determination of the ROIs may be performed in parallel with operation 610.

In some embodiments, the processing device 140 may determine the one or more ROIs in the second image one by one or determine at least two of the ROIs in the second image in parallel. For example, the processing device 140 may be used as including at least two independent threads each of which determines the ROIs one by one, and therefore at least two of the ROIs may be determined in the second image in parallel.

In some embodiments, at least two operations of the automatic determination of ROIs, the display of automatically determined ROIs, and the manual acceptance or modification of the automatically determined ROIs may be performed in parallel.

For example, immediately after a first ROI is automatically determined in the second image, regardless of whether the first ROI is displayed or the processing device 140 has received an acceptance or modification instruction related to the first ROI from a user, the processing device 140 may determine a second ROI. As another example, the processing device 140 may determine whether to keep the first ROI or update the first ROI based on a user instruction while continuing to perform the determination of a second ROI in parallel.

In some embodiments, the automatic determination of the one or more ROIs in the second image may be performed based on an estimate of a length of time for determining each of the one or more ROIs. In some embodiments, the length of time for determining an ROI may be determined by the processing device 140 or be preset by the user based on the characteristic of the tissue in the ROI and the algorithm for determining the ROI. The plan determination module 420 may rank the lengths of time, e.g., in an ascending order. The plan determination module 420 may automatically determine the one or more ROIs based on the ranking result. In this way, there may be at least one automatically determined ROI for the user to analyze as soon as possible. If it is determined that an ROI may take the processing device 140 a relatively long time to determine in the second image at first, the user may need to wait for a relatively long time, which may reduce the efficiency of the re-planning process in the adaptive radiation therapy.

In some embodiments, during the period in which the user decides whether to modify an automatically determined ROI, the processing device 140 may complete the determination of multiple ROIs in the second image. Therefore, after the user completes the modification of an ROI, there may be multiple automatically determined ROIs for the user to review or process or analyze. In some embodiments, the processing device 140 may rank the one or more automatically determined ROIs to be processed in a descending order based on an estimate of an amount of work or a length of time needed to modify each of the one or more automatically determined ROIs. The (estimated) amount of work or length of time needed to modify an ROI may have a correlation with the used algorithm to automatically determine the ROI and the structure of the tissue included in the ROI. The higher the accuracy of the used algorithm to automatically determine an ROI including the tissue, the shorter the length of time needed to modify the ROI may be. In some embodiments, the (estimated) amount of work or length of time needed to modify an ROI may be determined by the processing device 140 or be preset by the user based on the characteristic of the tissue in the ROI and/or the algorithm that is used in the automatic determination of the ROI. In some embodiments, the processing device 140 may cause the display of a list in which the automatically determined ROIs are ranked in a descending order based on the (estimated) amount of work or length of time needed to modify each ROI. In some embodiments, the user may be encouraged (but not forced) to review or modify the ROIs according to the ascending order in which ROIs with more (estimated) amounts of work or lengths of time for the user to perform review or modification thereof are ranked higher than ROIs with less (estimated) amounts of work or lengths of time for the user to perform review or modification. In some embodiments, the processing device 140 may allow the user to review or analyze the ROIs only according to the descending order in which the user needs to review or modify ROIs with more (estimated) amounts of work or lengths of time for the user to perform review or modification earlier than the user reviews or modifies other ROIs.

In this way, after the user finishes reviewing (e.g., accepting or modifying) an ROI, there may be at least one automatically determined ROI for the user to analyze; otherwise, after the user finishes reviewing an ROI, there may be no automatically determined ROI for the user to analyze, since the processing device 140 determines the ROIs in the ascending order of the length of time used to determine each ROI, which may reduce the efficiency of the re-planning process in the adaptive radiation therapy.

In some embodiments, the one or more ROIs in the second image may be determined using different techniques. Merely by way of example, the plan determination module 420 may automatically determine ROI A in the second image based on a segmentation algorithm. The plan determination module 420 may automatically determine ROI B in the second image based on a result of deformable registration between the first image and the second image (or referred to as a deformable registration result for brevity). The plan determination module 420 may automatically determine ROI C in the second image based on a rigid registration result between the first image and the second image. The plan determination module 420 may determine ROI D in the second image based on an instruction from the user. A technique used to automatically determine an ROI may be selected from a plurality of techniques based on one or more factors including, e.g., the anatomy of the tissue, organ, or structure where an ROI is to be determined. In some embodiments, the types of the ROIs to be determined may be included in the first radiation therapy plan. A technique used to determine an ROI may be selected based on the type of the ROI. For example, the ROI of tissue that needs to be protected from radiation, such as a lung, rectum, pancreas, etc., or a portion thereof, may be determined based on the segmentation algorithm. As another example, the ROI of tissue that is likely to undergo a change after radiation, such as the target object (e.g., tumor) or colon, etc., or a portion thereof, may be determined based on the deformable registration result. In some embodiments, the determination of different ROIs in the second image may be performed in parallel.

In some embodiments, multiple techniques for determining an ROI may be applied to a same location (e.g., same tissue) in the second image, from which different ROIs corresponding to the same tissue may be determined. The user may choose one determined ROI to review and other ROIs for the tissue may be deleted. For example, for certain tissue (e.g., a tumor) in the second image, the plan determination module 420 may determine ROI E based on a non-rigid deformable registration result, and determine ROI F using a rigid registration result. The user may be allowed to choose either one to review (e.g., accept or modify). Merely by way of example, the user may accept ROI E determined based on the non-rigid deformable registration result. Upon that, ROI F determined based on the rigid registration result may be deleted. In some embodiments, the determination of ROIs for same tissue in the second image using different techniques may be performed in parallel.

In 640, the processing device 140 (e.g., the plan determination module 420) may estimate a first dose distribution in the second image based on the first radiation therapy plan and the second image. The first dose distribution in the second image may be a distribution of a total dosage of radiations delivered to or received by the target object at the target structure (e.g., tumor) and the surrounding normal structure after the treatment fraction corresponding to the first radiation therapy plan. In some embodiments, the first dose distribution may be represented by a total dosage of radiations of each pixel/voxel in the second image. In some embodiments, the first dose distribution may be represented as pixel or voxel values of the pixels/voxels in the second image.

The plan determination module 420 may apply the treatment parameters of the first radiation therapy plan to the registered second image to generate the first dose distribution of the first radiation therapy plan. The determination of the first dose distribution may be similar to that of the distribution of the accumulated dose in the second image. See, e.g., operation 620 and the description thereof, which are not be repeated here.

In some embodiments, operations 620-640 are independent of each other. The processing device 140 may perform at least two of operations 620-640 in parallel.

In 650, the processing device 140 (e.g., the plan determination module 420) may estimate a second dose distribution in the one or more ROIs in the second image based on the first dose distribution. The second dose distribution in the second image may be a dosage of radiations delivered to or received by the one or more ROIs in the second image in the treatment fraction corresponding to the first radiation therapy. The second dose distribution may indicate the estimated radiation dose that is going to be delivered to each ROI in the second image if the treatment fraction is delivered to the target object based on the first radiation therapy plan (e.g., a part of the original whole treatment plan).

The second dose distribution may be estimated based on the first dose distribution, the one or more ROIs in the second image, and the distribution of the accumulated dose. For example, the processing device 140 may determine a third dose distribution in the second image by subtracting the distribution of the accumulated dose from the first dose distribution. The third dose distribution in the second image may be a distribution of a dosage of radiations delivered to or received by the target object at the target structure (e.g., tumor) and the surrounding normal structure in the treatment fraction corresponding to the first radiation therapy plan. In some embodiments, the third dose distribution may be represented by a dosage of radiations of each pixel/voxel in the second image. In some embodiments, the third dose distribution may be represented as pixel or voxel values of the pixels/voxels in the second image. The processing device 140 may determine the second dose distribution based on the third dose distribution (e.g., the subtraction result) and the one or more ROIs.

In some embodiments, the second dose distribution may include a dose-volume histogram (DVH) related to the second image. The processing device 140 may determine the DVH based on the first dose distribution and/or the first radiation therapy. A DVH may show a relationship between the received radiation dose and the volume of the target object in a treatment fraction. The DVH may facilitate the evaluation of different treatment fractions and/or corresponding radiation therapy plans. For example, the DVH may be configured to compare the delivered radiation doses from different treatment fractions.

In some embodiments, the plan determination module 420 may determine the delivered radiation dose in a treatment fraction for each voxel/pixel in the second image of the target object and generate a histogram, counting the number (or count) of voxels/pixels that receive a same radiation dose according to the first radiation therapy. In some embodiments, the processing device 140 may determine a DVH corresponding to each ROI in the second image. In some embodiments, in a DVH, the volume in the vertical axis and the dose in the horizontal axis may be displayed in absolute terms (e.g., cubic centimeters (cc), Gy) or in relative terms (e.g., % volume, % dose), depending on how the results are to be analyzed.

In some embodiments, the processing device 140 may display the first dose distribution based on the one or more ROIs. In some embodiments, the processing device 140 may display the second dose distribution. In some embodiments, the displaying of the first dose distribution may be performed in parallel with operation 650 or the displaying of the second dose distribution.

In 660, the processing device 140 (e.g., the plan determination module 420) may determine whether to keep using the first radiation therapy plan to treat the target object in the corresponding treatment fraction. The processing device 140 may determine whether the first radiation therapy plan satisfies one or more preset conditions based on the second dose distribution. For example, the one or more preset conditions may include the maximum dose to be delivered to or received by surrounding normal tissue in a treatment fraction, a total dose range to be delivered to or received by the target object in a treatment fraction, a dose range to be delivered to or received by the target structure (e.g., a tumor) of the target object in a treatment fraction, or the like, or any combination thereof. In some embodiments, the user may add one or more new preset conditions and/or modify at least one of the original preset conditions for the treatment fraction corresponding to the first radiation therapy plan. The processing device 140 may determine whether to keep using the first radiation therapy plan to treat the target object in the treatment fraction based further on the newly added and/or the modified preset conditions. In some embodiments, the one or more preset conditions may be determined by the processing device 140 and/or the user.

In 670, the processing device 140 (e.g., the plan determination module 420) may use the second radiation therapy plan to treat the target object in response to a determination that the first radiation therapy does not satisfy the one or more preset conditions.

In some embodiments, the second radiation therapy plan may be generated by the processing device 140 and/or the user based on the first radiation therapy plan, the second dose distribution, the one or more ROIs in the second image, and the one or more preset conditions.

In 680, the processing device 140 (e.g., the plan determination module 420) may use the first radiation therapy plan to treat the target object in response to a determination that the first radiation therapy satisfies the one or more preset conditions.

In some embodiments, the processing device 140 may perform the generation of the second radiation therapy plan and operation 660 in parallel. In this way, in response to a determination that the first radiation therapy does not satisfy the one or more preset conditions, the wait time for generating the second radiation therapy plan may be shortened, which may improve the efficiency of adaptive radiation therapy. It means that regardless of the determination result of operation 660, the processing device 140 may determine the second treatment plan to reduce idle time of the system 100 or the user; whether the second treatment plan is going to be used may depend on the determination result of operation 660.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 660 and 680 may be omitted.

FIG. 7 is a flowchart illustrating an exemplary process for determining a target radiation therapy plan according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150 and/or the storage 220) in the form of instructions (e.g., an application), and invoked and/or executed by the processing device 140 (e.g., the processor 210 illustrated in FIG. 2 and/or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 140 (e.g., the plan determination module 420) may determine the one or more ROIs in the second image. More descriptions of the determination of the ROIs in the second image may be found elsewhere in the present disclosure (e.g., operation 630 of the process 600 in FIG. 6, and the descriptions thereof).

In 720, the processing device 140 (e.g., the plan determination module 420) may generate a first intermediate plan by updating the first radiation therapy plan based on the one or more determined ROIs.

In some embodiments, the processing device 140 may determine the second dose distribution in the second image based on the one or more determined ROIs, and generate the first intermediate plan by updating the first radiation therapy plan based on the second dose distribution and one or more preset conditions. More descriptions of the determination of the second dose distribution and the first intermediate plan may be found elsewhere in the present disclosure (e.g., similar to operation 650 and 670 of the process 600 in FIG. 6, and the descriptions thereof).

In some embodiments, the processing device 140 may generate a DVH corresponding to the first intermediate plan based on the one or more automatically determined ROIs and the second dose distribution. More descriptions of the DVH may be found elsewhere in the present disclosure (e.g., similar to operation 650 of the process 600 in FIG. 6, and the descriptions thereof).

In some embodiments, the processing device 140 may divide the one or more automatically determined ROIs into a plurality of groups (e.g., N groups of ROIs, N is a positive integer). The processing device 140 may perform a plurality of iterations (e.g., N iterations) to generate the second radiation therapy plan based on the first intermediate plan. For example, at least one of the plurality of iterations may include operations 730-750.

In 730, the processing device 140 (e.g., the plan determination module 420) may receive an instruction related to reviewing (e.g., modifying or accepting) a $t^{th}$ (t=1, 2, 3 . . . , N) group of ROIs. The $t^{th}$ group of ROIs may include at least one of the one or more determined ROIs.

In some embodiments, the one or more determined ROIs may be divided into a plurality of groups (e.g., N groups of ROIs) based on an estimate of an amount of work or a length of time for manually modifying each ROI. For example, the one or more ROIs may be divided into 3 groups, such as the (estimated) lengths of time for manual modification being less than 3 minutes, between 3 minutes and 5 minutes, and more than 5 minutes. As another example, the one or more ROIs may be divided into 3 groups, such as the (estimated) amounts of work for manual modification being complex, moderate, and simple. More descriptions of the length of time for manually modifying an ROI may be found elsewhere in the present disclosure (e.g., operation 630 of the process 600 in FIG. 6, and the descriptions thereof).

In some embodiments, the processing device 140 may cause the display of a list in which the plurality of ROIs are ranked, e.g., in an ascending order based on the (estimated) amount of work or length of time needed to review each ROI. The user may be allowed or encouraged (but not forced) to review the ROIs according to the ranking result. In some embodiments, the processing device 140 may allow the user to review the ROIs only according to the ranking result, for example, in the ascending order in which the user needs to review or modify ROIs with less (estimated) amounts of work or lengths of time for the user to perform review or modification earlier than the user reviews or modifies other ROIs. In this way, the processing device 140 may update the first intermediate plan to generate the second intermediate plan as soon as possible. If it is determined that a group of the determined ROIs may take the user a relatively long time to review at first, the processing device 140 may be idle for a relatively long time (e.g., the wait time for generating the second intermediate plan based on the first reviewed group of ROIs may be relatively long), which may reduce the efficiency of the re-planning process in the adaptive radiation therapy.

More descriptions of the manual modification and/or acceptance of the ROI may be found elsewhere in the present disclosure (e.g., similar to operation 630 of the process 600 in FIG. 6, and the descriptions thereof), which are not repeated here.

In 740, the processing device 140 (e.g., the plan determination module 420) may process (e.g., update or keep) the $t^{th}$ group of ROIs based on the instruction.

In some embodiments, the user may provide an instruction to indicate that the one or more determined ROIs in the $t^{th}$ group of ROIs need to be modified or are acceptable. The plan determination module 420 may keep a determined ROI the $t^{th}$ group of ROIs based on a user instruction that the ROI is acceptable (or referred to as an acceptance instruction for brevity). The plan determination module 420 may update a determined ROI in the $t^{th}$ group of ROIs based on a user instruction that the ROI needs to be modified (or referred to as a modification instruction for brevity).

In 750, the processing device 140 (e.g., the plan determination module 420) may generate a $(t+1)^{th}$ intermediate plan based on the $t^{th}$ intermediate plan and the processed $t^{th}$ group of ROIs.

For example, the processing device 140 may process (e.g., update or keep) the second dose distribution in the second image determined in the previous iteration (e.g., the $(t-1)^{th}$ iteration) based on the processed $t^{th}$ group of ROIs, and generate the $(t+1)^{th}$ intermediate plan by processing (e.g., updating or keeping) the $t^{th}$ plan based on the processed second dose distribution and one or more preset conditions. More descriptions of the determination of the second dose distribution and the first intermediate plan may be found elsewhere in the present disclosure (e.g., similar to operation 650 and 670 of the process 600 in FIG. 6, and the descriptions thereof).

In some embodiments, the processing device 140 may generate a DVH corresponding to the $(t+1)^{th}$ intermediate plan based on the processed $t^{th}$ group of ROIs and the processed second dose distribution.

In some embodiments, the processing device 140 may perform operations 730 and 740 in parallel with operation 750. For example, after automatically processing the first group of ROIs in the second image, regardless of whether the processing device 140 finishes generating the second intermediate plan based on the processed first group ROIs, once the processing device 140 receives an instruction related to modifying or accepting the second group of ROIs from the user, the processing device 140 may process (e.g., accept or update) the second group of ROIs based on the instruction.

In some embodiments, the processing device 140 may perform operation 720 in parallel with the processing of the first group of ROIs based on the user's instruction. For example, the processing device 140 may generate the first intermediate plan based on the one or more automatically determined ROIs while receiving an instruction for reviewing (e.g., modifying or accepting) the first group of automatically determined ROIs from the user or processing (e.g., updating or keeping) the first group of automatically determined ROIs based on the user's instruction.

In 760, the processing device 140 (e.g., the plan determination module 420) may designate the intermediate plan generated in a last iteration of the plurality of iterations as the second radiation therapy plan.

In this way, during the process for reviewing the determined ROIs, the processing device 140 may continue to update the first radiation therapy plan in real time based on the latest reviewed ROIs. When all of the determined ROIs are reviewed (e.g., modified or accepted), the second radiation therapy plan is accordingly generated, which may take shorter time compared to performing the process for updating the first radiation therapy plan only after all of the ROIs are reviewed (e.g., modified or accepted).

In some embodiments, the process 600 and the process 700 may be combined to determine the target radiation therapy plan. For example, operations 630-650 may be replaced by the process 700. In some embodiments, if the user does not require the processing device 140 to perform the process 700, the user may turn off the process 700 through, for example, the I/O 230 and/or the I/O 350.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A method for generating an adaptive radiation therapy plan, implemented on a machine having one or more processors and one or more storage devices, the method comprising:

obtaining a first image related to one or more target objects generated by a first scan;

obtaining a first radiation therapy plan for treating the one or more target objects, the first radiation therapy plan being associated with the first image;

obtaining a second image related to the one or more target objects generated by a second scan, the second scan being performed later than the first scan; and determining, based on the first radiation therapy plan, the first image, and the second image, a target radiation therapy plan to treat the one or more target objects, the target radiation therapy plan being the first radiation therapy plan or a second radiation therapy plan associated with the second image, wherein determining the target radiation therapy plan includes at least one of the following processes:

a process for performing an operation for determining one or more regions of interest (ROIs) in the second image and an operation for determining an accumulated dose in the second image in parallel;

a process for performing an operation for estimating a first dose distribution in the second image based on the first radiation therapy plan in parallel with the operation for determining the one or more ROIs in the second image;

a process for performing an operation for automatically determining one or more second ROIs in the second image in parallel with at least one of an operation for receiving a first instruction for modifying or accepting one or more first ROIs that are automatically determined in the second image and an operation for processing the one or more first ROIs based on the first instruction;

a process for performing an operation for determining whether to generate the second radiation therapy plan or continue using the first radiation therapy plan to treat the one or more target objects in parallel with an operation for generating the second radiation therapy plan; or a process for performing an operation for generating the second radiation therapy plan in parallel with at least one of an operation for receiving an instruction for modifying or accepting one or more eighth automatically determined ROIs and an operation for processing the one or more eighth automatically determined ROIs based on the instruction for modifying or accepting the one or more eighth automatically determined ROIs.

2. The method of claim 1, wherein the determining the target radiation therapy plan includes:

generating a registration result by performing image registration between the first image and the second image;

determining the one or more ROIs in the second image based on the registration result;

determining the accumulated dose in the second image based on the registration result, the accumulated dose having been delivered to the one or more target objects; and estimating a first dose distribution in the second image based on the first radiation therapy plan, wherein an operation for determining the one or more ROIs in the second image based on the registration result and an operation for determining the accumulated dose in the second image based on the registration result are performed in parallel; or an operation for estimating the first dose distribution in the second image based on the first radiation therapy plan is performed in parallel with at least one of an operation for generating the registration result by performing the image registration between the first image and the second image and the operation for determining the one or more ROIs in the second image based on the registration result.

3. The method of claim 1, wherein determining the target radiation therapy plan includes:

estimating a length of time for determining each of one or more seventh ROIs in the second image;

ranking the lengths of time; and automatically determining the one or more seventh ROIs in the second image based on the ranking result.

4. The method of claim 1, wherein determining the target radiation therapy plan includes:

automatically determining a third ROI in the second image based on a segmentation algorithm;

automatically determining a fourth ROI in the second image based on a deformable registration result by performing a deformable registration between the first image and the second image; and automatically determining a fifth ROI in the second image based on a rigid registration result by performing a rigid registration between the first image and the second image, wherein at least two of an operation for automatically determining the third ROI based on the segmentation algorithm, an operation for automatically determining the fourth ROI based on the deformable registration result by performing the deformable registration between the first image and the second image, and an operation for automatically determining the fifth ROI based on the rigid registration result by performing the rigid registration between the first image and the second image are performed in parallel.

5. The method of claim 1, wherein the determining the target radiation therapy plan includes:

estimating a first dose distribution in the second image based on the first radiation therapy plan;

determining a dose volume diagram (DVH) based on the first dose distribution and the one or more ROIs;

determining, based on the estimated first dose distribution or the DVH in the second image, whether to generate the second radiation therapy plan associated with the second image or continue using the first radiation therapy plan to treat the one or more target objects; and generating the second radiation therapy plan based on the first radiation therapy plan, a second dose distribution in the one or more ROIs in the second image, one or more preset conditions and the one or more ROIs in the second image, the one or more preset conditions including at least one of a maximum dose to be delivered to or received by surrounding normal tissue in a treatment fraction, a total dose range to be delivered to or received by the one or more target objects in the treatment fraction, or a dose range to be delivered to or received by a target structure of the one or more target objects in the treatment fraction, wherein an operation for determining, based on the estimated first dose distribution or the DVH in the second image, whether to generate the second radiation therapy plan associated with the second image or continue using the first radiation therapy plan to treat the one or more target objects is performed in parallel with an operation for generating the second radiation therapy plan based on the first radiation therapy plan, the second dose distribution, the one or more preset conditions and the one or more ROIs in the second image.

6. The method of claim 5, further comprising:

displaying the first dose distribution in the second image based on the one or more ROIs; and displaying the DVH;

wherein an operation for displaying the first dose distribution in the second image based on the one or more ROIs is performed in parallel with at least one of an operation for estimating the DVH based on the first dose distribution and the one or more ROIs and an operation for displaying the DVH.

7. The method of claim 1, wherein the determining the target radiation therapy plan includes:

automatically determining one or more sixth ROIs in the second image;

generating a first intermediate plan by updating, based on the one or more determined sixth ROIs, the first radiation therapy plan;

updating the first intermediate plan by performing a plurality of iterations, a $t^{th}$ ($t=1, 2, 3 \ldots$) iteration of the plurality of iterations including:

receiving a second user instruction for modifying or accepting a $t^{th}$ group of ROIs, the $t^{th}$ group of ROIs including at least one of the one or more determined sixth ROIs;

processing the $t^{th}$ group of ROIs based on the second user instruction; and generating a (t+1)$^{th}$ intermediate plan based on the t$^{th}$ intermediate plan and the processed t$^{th}$ group of ROIs; and designating the intermediate plan generated in a last iteration of the plurality of iterations as the second radiation therapy plan.

8. The method of claim 7, wherein the determining the target radiation therapy plan further includes:

estimating an amount of work for manually modifying each of the one or more sixth ROIs that are automatically determined;

assigning the one or more sixth ROIs into a plurality of groups based on the amounts of work for manually modifying the one or more ROIs; and generating an instruction that prompts a user to modify, based on the group assignments, the one or more sixth ROIs.

9. The method of claim 7, wherein an operation for generating the first intermediate plan by updating, based on the one or more determined sixth ROIs, the first radiation therapy plan is performed in parallel with at least one of an operation for receiving the instruction for modifying or accepting the first group of ROIs and an operation for processing the first group of ROIs based on the instruction for modifying or accepting the first group of ROIs; or an operation for generating the (t+1)th intermediate plan based on the tth intermediate plan and the processed tth group of ROIs is performed in parallel with at least one of an operation for receiving the instruction for modifying or accepting the (t+1)th group of ROIs and an operation for processing the (t+1)th group of ROIs based on the instruction for modifying or accepting the (t+1)th group of ROIs.

10. The method of claim 1, wherein at least one of an operation for obtaining the first image and an operation for obtaining the first radiation therapy plan is performed during the second scan.

11. The method of claim 1, wherein two or more operations performed in parallel start or are finished at a same time or at different times.

12. A system for generating an adaptive radiation therapy plan, comprising:

at least one storage device storing a set of instructions; and at least one processor in communication with the at least one storage device, wherein when the at least one processor executes the set of instructions, the system is caused to perform operations including:

obtaining a first image related to one or more target objects generated by a first scan;

obtaining a first radiation therapy plan for treating the one or more target objects, the first radiation therapy plan being associated with the first image;

obtaining a second image related to the one or more target objects generated by a second scan, the second scan being performed later than the first scan; and determining, based on the first radiation therapy plan, the first image, and the second image, a target radiation therapy plan to treat the one or more target objects, the target radiation therapy plan being the first radiation therapy plan or a second radiation therapy plan associated with the second image, wherein determining the target radiation therapy plan includes at least one of the following processes:

a process for performing an operation for determining one or more regions of interest (ROIs) in the second image and an operation for determining an accumulated dose in the second image in parallel;

a process for performing an operation for estimating a first dose distribution in the second image based on the first radiation therapy plan in parallel with the operation for determining the one or more ROIs in the second image;

a process for performing an operation for automatically determining one or more second ROIs in the second image in parallel with at least one of an operation for receiving a first instruction for modifying or accepting one or more first ROIs that are automatically determined in the second image and an operation for processing the one or more first ROIs based on the first instruction;

a process for performing an operation for determining whether to generate the second radiation therapy plan or continue using the first radiation therapy plan to treat the one or more target objects in parallel with an operation for generating the second radiation therapy plan; or a process for performing an operation for generating the second radiation therapy plan in parallel with at least one of an operation for receiving an instruction for modifying or accepting one or more eighth automatically determined ROIs and an operation for processing the one or more eighth automatically determined ROIs based on the instruction for modifying or accepting the one or more eighth automatically determined ROIs.

13. The system of claim 12, wherein the determining the target radiation therapy plan includes:

generating a registration result by performing image registration between the first image and the second image;

determining the one or more ROIs in the second image based on the registration result;

determining the accumulated dose in the second image based on the registration result, the accumulated dose having been delivered to the one or more target objects; and estimating a first dose distribution in the second image based on the first radiation therapy plan, wherein an operation for determining the one or more ROIs in the second image based on the registration result and an operation for determining the accumulated dose in the second image based on the registration result are performed in parallel; or an operation for estimating the first dose distribution in the second image based on the first radiation therapy plan is performed in parallel with at least one of an operation for generating the registration result by performing the image registration between the first image and the second image and the operation for determining the one or more ROIs in the second image based on the registration result.

14. The system of claim 11, wherein determining the target radiation therapy plan includes:

estimating a length of time for determining each of one or more seventh ROIs in the second image;

ranking the lengths of time; and automatically determining the one or more seventh ROIs in the second image based on the ranking result.

15. The system of claim 12, wherein determining the target radiation therapy plan includes:

automatically determining a third ROI in the second image based on a segmentation algorithm;

automatically determining a fourth ROI in the second image based on a deformable registration result by performing a deformable registration between the first image and the second image; and automatically determining a fifth ROI in the second image based on a rigid registration result by performing a rigid registration between the first image and the second image, wherein at least two of an operation for automatically determining the third ROI based on the segmentation algorithm, an operation for automatically determining the fourth ROI based on the deformable registration result by performing the deformable registration between the first image and the second image, and an operation for automatically determining the fifth ROI based on the rigid registration result by performing the rigid registration between the first image and the second image are performed in parallel.

16. The system of claim 12, wherein the determining the target radiation therapy plan includes:
    estimating a first dose distribution in the second image based on the first radiation therapy plan;
    determining a dose volume diagram (DVH) based on the first dose distribution and the one or more ROIs;
    determining, based on the estimated first dose distribution or the DVH in the second image, whether to generate the second radiation therapy plan associated with the second image or continue using the first radiation therapy plan to treat the one or more target objects; and
    generating the second radiation therapy plan based on the first radiation therapy plan, a second dose distribution in the one or more ROIs in the second image, one or more preset conditions and the one or more ROIs in the second image, the one or more preset conditions including at least one of a maximum dose to be delivered to or received by surrounding normal tissue in a treatment fraction, a total dose range to be delivered to or received by the one or more target objects in the treatment fraction, or a dose range to be delivered to or received by a target structure of the one or more target objects in the treatment fraction, wherein
        an operation for determining, based on the estimated first dose distribution or the DVH in the second image, whether to generate the second radiation therapy plan associated with the second image or continue using the first radiation therapy plan to treat the one or more target objects is performed in parallel with an operation for generating the second radiation therapy plan based on the first radiation therapy plan, the second dose distribution, the one or more preset conditions and the one or more ROIs in the second image.

17. The system of claim 12, wherein the determining the target radiation therapy plan includes:
    automatically determining one or more sixth ROIs in the second image;
    generating a first intermediate plan by updating, based on the one or more determined sixth ROIs, the first radiation therapy plan;
    updating the first intermediate plan by performing a plurality of iterations, a $t^{th}$ (t=1, 2, 3 ... ) iteration of the plurality of iterations including:
        receiving a second user instruction for modifying or accepting a $t^{th}$ group of ROIs, the $t^{th}$ group of ROIs including at least one of the one or more determined sixth ROIs;
        processing the $t^{th}$ group of ROIs based on the second user instruction; and
        generating a $(t+1)^{th}$ intermediate plan based on the $t^{th}$ intermediate plan and the processed $t^{th}$ group of ROIs; and
    designating the intermediate plan generated in a last iteration of the plurality of iterations as the second radiation therapy plan.

18. The system of claim 17, wherein the determining the target radiation therapy plan further includes:
    estimating an amount of work for manually modifying each of the one or more sixth ROIs that are automatically determined;
    assigning the one or more sixth ROIs into a plurality of groups based on the amounts of work for manually modifying the one or more ROIs; and
    generating an instruction that prompts a user to modify, based on the group assignments, the one or more sixth ROIs.

19. The system of claim 17, wherein an operation for generating the first intermediate plan by updating, based on the one or more determined sixth ROIs, the first radiation therapy plan is performed in parallel with at least one of an operation for receiving the instruction for modifying or accepting the first group of ROIs and an operation for processing the first group of ROIs based on the instruction for modifying or accepting the first group of ROIs; or
    an operation for generating the (t+1)th intermediate plan based on the tth intermediate plan and the processed tth group of ROIs is performed in parallel with at least one of an operation for receiving the instruction for modifying or accepting the (t+1)th group of ROIs and an operation for processing the (t+1)th group of ROIs based on the instruction for modifying or accepting the (t+1)th group of ROIs.

20. A non-transitory computer readable medium, comprising at least one set of instructions for generating an adaptive radiation therapy plan, wherein when executed by one or more processors of a computing device, the at least one set of instructions causes the computing device to perform a method, the method comprising:
    obtaining a first image related to one or more target objects generated by a first scan;
    obtaining a first radiation therapy plan for treating the one or more target objects, the first radiation therapy plan being associated with the first image;
    obtaining a second image related to the one or more target objects generated by a second scan, the second scan being performed later than the first scan; and
    determining, based on the first radiation therapy plan, the first image, and the second image, a target radiation therapy plan to treat the one or more target objects, the target radiation therapy plan being the first radiation therapy plan or a second radiation therapy plan associated with the second image, wherein determining the target radiation therapy plan includes at least one of the following processes:
        a process for performing an operation for determining one or more regions of interest (ROIs) in the second image and an operation for determining an accumulated dose in the second image in parallel;
        a process for performing an operation for estimating a first dose distribution in the second image based on the first radiation therapy plan in parallel with the operation for determining the one or more ROIs in the second image;

a process for performing an operation for automatically determining one or more second ROIs in the second image in parallel with at least one of an operation for receiving a first instruction for modifying or accepting one or more first ROIs that are automatically determined in the second image and an operation for processing the one or more first ROIs based on the first instruction;

a process for performing an operation for determining whether to generate the second radiation therapy plan or continue using the first radiation therapy plan to treat the one or more target objects in parallel with an operation for generating the second radiation therapy plan; or a process for performing an operation for generating the second radiation therapy plan in parallel with at least one of an operation for receiving an instruction for modifying or accepting one or more eighth automatically determined ROIs and an operation for processing the one or more eighth automatically determined ROIs based on the instruction for modifying or accepting the one or more eighth automatically determined ROIs.

* * * * *